United States Patent
Weisman et al.

(10) Patent No.: US 6,630,164 B2
(45) Date of Patent: Oct. 7, 2003

(54) DUTASTERIDE TO PREVENT AND TREAT ATHEROSCLEROSIS

(76) Inventors: Kenneth Weisman, 30 Springton Pointe Dr., Newtown Square, PA (US) 19073; Michael E. Goldberg, 20 Aspen Dr., Ivyland, PA (US) 18974

( * ) Notice: Subject to any disclaimer, the term of this patent is extended or adjusted under 35 U.S.C. 154(b) by 47 days.

(21) Appl. No.: 09/851,454

(22) Filed: May 8, 2001

(65) Prior Publication Data

US 2001/0048942 A1 Dec. 6, 2001

Related U.S. Application Data

(60) Provisional application No. 60/202,425, filed on May 9, 2000.

(51) Int. Cl.$^7$ .............................. A61K 9/14; A61K 9/20; A61F 2/00

(52) U.S. Cl. ........................ 424/464; 424/423; 424/449; 424/455; 424/489; 514/824; 514/937

(58) Field of Search ................................. 424/464, 465, 424/489, 423, 455, 443, 445, 447, 449

(56) References Cited

FOREIGN PATENT DOCUMENTS

| WO | WO 96/08239 | * | 3/1996 | .......... A61K/31/00 |

* cited by examiner

*Primary Examiner*—James M. Spear
(74) *Attorney, Agent, or Firm*—Caesar, Rivise, Bernstein, Cohen & Pokotilow, Ltd.

(57) ABSTRACT

A method of decreasing atherosclerosis and its complications including but not limited to myocardial infarction, stroke, and peripheral vascular disease comprising administering to a human or animal an amount of dutasteride sufficient to decrease atherosclerosis and its complications.

3 Claims, No Drawings

DUTASTERIDE TO PREVENT AND TREAT ATHEROSCLEROSIS

This application claims the benefit of the filing date of May 9, 2000 of Provisional Patent Application Ser. No. 60/202,425.

BACKGROUND OF THE INVENTION

There are many steps in the biosynthesis and utilization by the tissues of testosterone. Testosterone is made mostly in the testicles. A lesser amount is made in the adrenals. Production is stimulated by secretion of GnRH or LHRH by the brain, which causes secretion of luteinizing hormone (LH) by the pituitary, which causes the testicles to make testosterone. Testosterone then flows into the blood stream and is absorbed by the target cells. Here it binds to a receptor and is transported into the cell and converted to dihydrotestosterone. This is bound and carried to the nucleus of the cell where it redirects cellular activity by turning on and off DNA. Hormonal manipulation is a term which refers to the reduction of testosterone or its effects by blocking any step in the above process in order to gain a desired effect. Until now the uses of hormonal manipulation include for example treating prostatic carcinoma, and treatment for baldness.

The present invention involves the use of hormonal manipulations in the prevention and treatment of atherosclerosis, including coronary heart disease, stroke, and peripheral vascular disease, We have already discovered as reflected by our patents that certain 5-alpha reductase inhibitors (finasteride) are effective (U.S. Pat. No. 6,090,409) for treating and preventing atherosclerosis and its complications, including coronary artery heart disease. Several LHRH agonists; Leuprolide (U.S. Pat. No. 6,099,851) and Goserelin.(U.S. Pat. No. 6,140,315), which inhibit testosterone metabolism at another step have also shown to be effective.

For instance, leuprolide acetate is one of the compounds we previously discovered being effective in the prevention of such cardiac events. Leuprolide acetate is a synthetic nonapeptide of naturally occurring gonadotropin-releasing hormone (GnRH or LH-RH), the chemical name is 5-oxo-L-prolyl-L-histidyl-L-tryptophyl-L-seryl-L-tyrosyl-D-leucyl-L-leucyl-L-arginyl-N-ethyl-L-prolinamide acetate salt sold under the trade name Lupron or Lupron Depot, as identified by U.S. Pat. No. 4,897,256, the entire disclosure in incorporated by reference herein, is known for use in the treatment of prostatic carcinoma. Leuprolide is known to decrease levels of LHRH, LH and Testosterone (a sex hormone).

Another compound we previously discovered as being effective in the prevention of such cardiac events is Goserelin acetate. Goserelin Acetate is a synthetic decapeptide analogue of LHRH or GnRH, is chemically described as an acetate salt of [D-Ser(Bu.sup.t).sup.6 Azygly.sup.10 ] LHRH. Its chemical structure is pyro-Glu-His-Trp-Ser-Tyr-D-Ser(Bu.sup.t)-Leu-Arg-Pro-Azgly-NH2 acetate [C59H84N18O14 (C2H4O2) sold under the trademark Zoladex, as identified by the U.S. Pat. No. 5,510,460, the entire disclosure is incorporated by reference herein, is known for the use in treatment of prostatic carcinoma. Goserelin acetate is known to reduce levels of GnRH or LHRH, and Testosterone, a sex hormone.

Finasteride, a synthetic 4-azasteroid compound. 4-azaandrost-1-ene-17-carboxamide, N-(1,1-dimethylethyl)-3-oxo-(5a 17B)-, sold under the trade name Proscar by Merck and Co., as identified by U.S. Pat. No. 5,175,155, the entire disclosure is incorporated by reference herein, is known for use in treatment of benign prostatic hypertrophy (BPH). Finasteride is known to inhibit testosterone metabolism by blocking conversion of testosterone to dihydrotestosterone by blocking 5-alpha-reductase. Finasteride is yet another compound we previously discovered as being effective in the prevention of cardiac events.

Now, we have discovered the existence of dutasteride (GI 198745), a dual 5-alpha reductase inhibitor chemical formula: (5alpha, 17 beta)-N-[2, 5-bis(trifluoromethyl)phenyl]-2-oxo-4-azaandrost-1-ene-17-carboximide is formally known for use in treatment of benign prostatic hyperplasia, manufacturer Glaxo Wellcome. Based on our studies of other 5-alpha reductase inhibitors, and of our studies of other compounds which decrease testosterone secretion by other means, we believe that dutasteride should be effective in preventing and treating atherosclerosis and myocardial infarction.

The data which leads us to conclude that suppression of testosterone metabolism can result in lower rates of atherosclerosis and its complications including coronary artery disease is presented below:

It was observed that patients to whom finasteride was being administered for treatment of benign prostatic hypertrophy seemed to have a lower incidence of atherosclerosis and heart disease.

Finasteride was being administered at a dosage of a single oral 5 mg tablet a day. This is the same tablet used in treatment of BPH as disclosed in U.S. Pat. No. 5,175,155 and such dosage applies in the present invention. However, use of a 2 mg or 10 mg oral tablet is contemplated.

Two studies were undertaken to determine whether finasteride was, in fact, effective in lessening the incidence of heart disease and other complications of atherosclerosis.

The result of the first study is as follows; A list of patients diagnosed with benign prostatic hypertrophy in late 1992 and 1993 was located. Treatment had been initiated with either finasteride or another oral agent of a different class (alpha-blocker). Patients were then contacted and an interval history was taken. In the control group of 45 subjects, 7 events (either cardiac bypass or heart attack) occurred in 6 subjects over 288 subject-years. In the finasteride treated group of 22 subjects there were no events over 61 subject-years. (Some patients had discontinued the use of finasteride, and only those on the drug for at least a year were considered.) We believe significantly more events occurred in the control group compared to the finasteride treated group. (95% Cl equal to 0.65% to 4.2%)

In the second study patients of the practice were given a questionnaire. Various patients had been treated with finasteride for varying lengths of time. Only those on the drug for at least one year were considered. The average time on finasteride was 3 years. The number of cardiac events occurring in the patients taking finasteride was only 4 events over 242 patient-years. (1.6%/yr.) In the control group 26 events occurred in the 3 years prior over 732 patient-years. (3.5%/yr.)

The 45% decrease observed in cardiac events is believed to be significant. (90% Cl equal to 1.4% to 3.7%)

Another retrospective study was performed which compared the rates of patient reported heart attack in several groups 1—control group of males entering the urology office for any routine complaint. 2—a group of prostate cancer patients treated with Leuprolide acetate, a LHRH inhibitor. 3—a group of prostate cancer patients treated with Goserelin acetate (Zoladex), a LHRH inhibitor. 4—a group of prostate cancer patients not treated with hormonal manipulation (neither Leuprolide or Goserelin). 5—all patients on LHRH inhibitors (group 2+group 3).

The patients on either Leuprolide or Goserelin were treated with the recommended doses indicated for the treatment of prostatic carcinoma, at either one or three month intervals depending on the preparation used. Leuprolide was dosed at 7.5 mg monthly (single intramuscular injection) or at 22.5 mg at 3 month intervals (single intramuscular injection). Goserelin was dosed at 3.6 mg monthly or at a dose of 10.8 mg at 3 month intervals (subcutaneous injection).

The various groups of office patients were evaluated by chart review. In groups 2 and 3 only those on drug for at least one year were considered. Cardiac event is defined either the history of a heart attack or occurrence of coronary artery bypass or angioplasty. In control groups only events occurring in the 3 years prior to the questionnaire are charted. The results were as follows:

|  | Cardiac Events | No Patients | Subject Years | Events/Year |
| --- | --- | --- | --- | --- |
| Group 1 (control no cancer) | 247 | 26 | 741 | .0351 |
| Group 4 (control cancer patients) | 69 | 6 | 207 | .0290 |
| Total Control (Groups 1 + 4) | 316 | 32 | 948 | .0338 |
| Group 2 (Lupron) | 28 | 1 | 118 | .00847 |
| Group 3 (Zoladex) | 25 | 1 | 62 | .0161 |
| Group 6 (antiLHRH) groups 2 + 3 | 53 | 2 | 180 | .0111 |

The observed difference between the proportions of Total Control vs Group 6 (LHRH) is 0.0226. 95% Confidence Interval for the difference between the proportions is 0.00350 to 0.0418. Patients treated with LHRH inhibitors had fewer heart attacks than controls.

The observed difference between the proportions of Group 2 (Lupron) and Total Control is 0.253. 95% Confidence Interval for the difference between the proportions is 0.00514 and 0.0454. Patients treated with Leuprolide acetate had fewer heart attacks than controls.

The observed difference between the proportions of Group 3 and Total Control is 0.0177. Patients treated with Goserelin (Zoladex) had fewer heart attacks than controls.

Without further elaboration the foregoing will so fully illustrate our invention that others, may, by applying current future knowledge, adopt the same for use under various conditions of service.

What is claimed is:

1. A method of decreasing atherosclerosis and its complications including diseases selected from the group consisting of myocardial infarction, stoke, and peripheral vascular disease, said method comprising administering to a human or animal in need thereof an amount of dutasteride in an effective amount to decrease atherosclerosis and its complications.

2. The method in claim 1 wherein the effective amount of dutasteride is 0.5 mg orally daily administered as a tablet.

3. The invention in claim 1 wherein the effective amount of dutasteride is administered as a tablet, suspension, or pellet, which may be given orally or as intramuscular injections, or administered as subcutaneous pellets or cutaneous patches or as a liquid, forming a solution or dispersion using an appropriate solvent or solvents with the intent of accomplishing systemic absorption of the drug.

* * * * *